United States Patent
Gutsche et al.

(10) Patent No.: US 7,825,277 B2
(45) Date of Patent: Nov. 2, 2010

(54) PROCESS FOR THE OZONOLYSIS OF UNSATURATED COMPOUNDS

(75) Inventors: Bernhard Gutsche, Hilden (DE); Stefan Franzen, Kamen (DE); Markus Kloeker, Duesseldorf (DE)

(73) Assignee: Cognis IP Management GmbH, Duesseldorf (DE)

( * ) Notice: Subject to any disclaimer, the term of this patent is extended or adjusted under 35 U.S.C. 154(b) by 787 days.

(21) Appl. No.: 11/801,385

(22) Filed: May 9, 2007

(65) Prior Publication Data

US 2007/0276165 A1    Nov. 29, 2007

(30) Foreign Application Priority Data

May 9, 2006    (DE)    ........................ 10 2006 021 438

(51) Int. Cl.
*C07C 51/16* (2006.01)
*C07C 45/00* (2006.01)

(52) U.S. Cl. ........................ 562/545; 562/544; 568/354

(58) Field of Classification Search ................ 562/544, 562/545; 568/354
See application file for complete search history.

(56) References Cited

U.S. PATENT DOCUMENTS

| | | | |
|---|---|---|---|
| 2,813,113 | A | 11/1887 | Goebel et al. |
| 5,883,269 | A | 3/1999 | Rebrovic |
| 2005/0010069 | A1* | 1/2005 | Fitchett et al. .............. 568/959 |

FOREIGN PATENT DOCUMENTS

| | | |
|---|---|---|
| CA | 2247662 A1 | 3/1999 |
| DE | 1 103 308 | 3/1961 |
| DE | 2 311 532 A | 3/1973 |
| DE | 34 40 620 A1 | 5/1986 |
| EP | 0 903 174 A1 | 3/1999 |
| GB | 1 429 944 A | 3/1976 |
| JP | 2004-285001 A | 10/2004 |
| JP | 2006-239640 A | 9/2006 |
| SU | 368 228 A | 1/1973 |
| WO | WO 95/21809 A1 | 8/1995 |
| WO | WO 02/064498 A1 | 8/2002 |
| WO | WO 2007/072097 A2 | 6/2007 |

OTHER PUBLICATIONS

Johnson et al., Reductive ozonolysis for Monoenoic Fatty Acid Strutured Determination in the Microreactor Apparatus (Journal of the American Oil Chemists' Society (1972), 49 (2), 98-100.*
Naudet et al., "Über die Ozonolyse der Ölsäure", Fette, Seifen, Anstrichmittel, vol. 62, (1960), pp. 1110-1112.
Pryde et al., "The Ozonization of Methyl Oleate", J. Org. Chem., vol. 25, (Apr. 1960), pp. 618-621.
Pryde et al., "Selective Hydrogenation of Methyl Oleate Ozonolysis Products by Palladium in Pyridine-Methanol Solvent", J. Org. Chem., vol. 27, (Sep. 1962), pp. 3055-3059.
Moore et al., "A Comparison of Participating Solvents During Ozonization", The Journal of the American Oil Chemists' Society, vol. 42, (Oct. 1965), pp. 894-898.
R.W. Johnson, Dibasic Fatty Acids in Fatty Acids in Industry, Marcel Dekker, 1989 (reciting entire book—not enclosed).
Jähnisch et al., "Chemie in Mikrostrukturreaktoren", Angewandte Chemie, vol. 116, (2004), pp. 410-451.
Angell et al., "Silicon Micromechanical Devices", Scientific American, vol. 248, No. 4, (Apr. 1983), pp. 44-55.
Burns et al., "Development of a Microreactor for Chemical Production", Trans Icheme, vol. 77, Part A, (May 1999), pp. 206-211.
Winnacker, Küchler: "Chemische Technik: Prozesse und Produkte" 2004, R. Dittmeyer, W. Keim, G. Kreysa, A. Oberholz, Wiley-VCH Verlag Gmbh & Co. KGAA, Weinheim (DE), Bd. 2, Seiten 759-819, XP002448664.
J. Kobayashi et al.: "A Microfluidic Device for Conducting Gas-Liquid-Solid Hydrogenation Reactions" Science, Bd. 304, 2004, Seiten 1305-1308, XP002448662.
Wada, Yasuhiro et al: "Flow Distribution and Ozonolysis in Gas-Liquid Multichannel Microreactors" Industrial & Engineering Chemistry Research Bd. 45, Nr. 24, 2006, Seiten 8036-8042, XP002448663.

* cited by examiner

*Primary Examiner*—Jafar Parsa

(57) ABSTRACT

A process for the ozonolysis of unsaturated starting materials, which is characterized in that the reaction is carried out in a structured reactor.

20 Claims, No Drawings

PROCESS FOR THE OZONOLYSIS OF UNSATURATED COMPOUNDS

CROSS-REFERENCE TO RELATED APPLICATIONS

This application claims priority under 35 U.S.C. §119 from German Patent Application No. 102006021438.2, filed May 9, 2006, the entire disclosure of which is hereby incorporated by reference.

BACKGROUND OF THE INVENTION

1. Field of the Invention

This invention relates generally to ozonolysis and, more particularly, to a process for the oxidation of unsaturated compounds which is carried out in structured reactors.

2. Background and Related Art

The ozonolysis of olefinic starting materials is among the standard processes of organic chemistry and, accordingly, is comprehensively described in literature and patent specifications, cf., for example, the articles by Naudet and Pasero in Fette, Seifen, Anstrichmittel 62, 1110 (1960), Pryde et al. in J. Org. Chem. 25, 618 (1960) and ibid., 27, 3055 (1962), Moore et al. in J. Americ. Oil. Chem. Soc. 42, 894 (1965), and U.S. Pat. No. 2,813,113 (Goebel et al.). In the first part of the reaction, a gas/liquid reaction of ozone with the olefinic starting material, ozonides are formed as unstable intermediate products. Water-containing substances [DE-OS 2311532] or organic substances [U.S. Pat. No. 5,883,269 (Rebrovic)] are normally added to dilute the olefinic reactants. This is associated on the one hand with the high viscosity of the ozonides formed (cf., Naudet and Pasero in Fette, Seifen, Anstrichmittel 62, op cit) and on the other hand with the control of reactivity [see U.S. Pat. No. 5,883,269]. In the case of organic solvents, substances formed in the subsequent oxidation or reduction of the ozonization products may advantageously be used. The addition of water may be of advantage in terms of suppressing the formation of unwanted secondary products. In the case of oxidative ozonolysis where the ozonization products formed as intermediates are oxidized, ketones or carboxylic acids are formed. The oxidation of the intermediate products is described, for example, in Published International Application WO 95/21809 A1. If the intermediate products are cleaved by reduction, aldehydes are obtained [see German Offenlegungsschrift DE-OS 3440620].

However, the disadvantage of the known processes is that they need improving both in regard to volume/time yield and in regard to selectivity. In addition, in view of the highly exothermic nature of the known processes, uneven temperature stress is encountered time and again in conventional reactors, resulting in variable, not always satisfactory product quality and, above all, product color. Moreover, the danger of hot-spots through inadequate heat dissipation is a safety risk because the ozonization products are unstable and can decompose explosively. Since the dissipation of heat in conventional reactors is limited, the ozone content is generally kept relatively low, typically at around 2% [cf., R. W. Johnson, "Dibasic Fatty Acids in Fatty Acids in Industry", Marcel Dekker, 1989]. The effect of this is that considerable amounts of gas are circulated and have to be correspondingly purified [DE-AS 1,103,308]. The circulation and treatment of the recycled gas is equipment- and energy-intensive and affects the economy of the process, as does the alternative use of fresh gas for producing the ozone instead of recycling. In order to reduce the risk of spontaneous ignition or explosion in the reactor, air is also used besides high-purity oxygen as the starting gas for producing ozone, which, unfortunately, is a disadvantage in regard to the formation of nitrogen oxides. In addition, carbon dioxide is also used for ozone production [see Published International Application WO 02/064498 A1].

Also, in conventional processes, volatile secondary products are formed to a relatively large extent in both reaction steps, adding considerably to the waste gas burden and again affecting economy.

Accordingly, the complex problem addressed by the present invention was safely, to avoid or reduce the above-mentioned disadvantages of the prior art. More particularly, the invention set out to provide a process which would provide the ozonolysis products in higher volume/time yields and with greater selectivity and which would simplify the technical aspect of the process. Above all, the quantity of ozone in the reaction mixture would be increased, without compromising safety.

SUMMARY OF THE INVENTION

The present invention relates to a process for the ozonolysis of unsaturated starting materials, which is characterized in that the reaction is carried out in a structured reactor.

It has surprisingly been found that carrying out the ozonolysis in a structured reactor, preferably a micro(structure) reactor, has many advantages and is clearly superior to the known processes in the following respects:

- Through the improved exchange of heat and material, the significantly improved dissipation of the heat of reaction attributable to the high surface-to-volume ratio and the defined flow regimes and forms, higher volume/time yields, higher selectivities and improved product quality are obtained.
- In addition, by virtue of the higher selectivities, the quantity of volatile and nonvolatile secondary products formed is smaller, leading to the simplification of subsequent cleaning or waste air treatment steps.
- The composition of the reactants can be selected independently of the explosion limits. In particular, the concentration of ozone in the starting gas can be increased because the improved dissipation of heat means that local, product-discoloring hot-spots are avoided. In addition, the volume of recycle gas is also reduced in this way.

DETAILED DESCRIPTION OF THE INVENTION

Structured Reactors and Microreactor Systems

A preferred embodiment of the present invention makes use of the knowledge that structured reactors enable the ozonolysis of unsaturated starting materials to be carried out irrespective of the explosion limits providing the reaction channels have diameters that do not exceed the "limiting gap width", i.e., the maximum diameter of a reactor at which an explosion-induced flame still goes out automatically. This makes it possible to use any mixtures of ozone and unsaturated substrates and still operate the reactor safely, even in the explosion range. As explained above, it is thus possible for the first time to operate with high ozone concentrations and thus to limit the volume of recycle gas. It is obvious that this represents a significant economic advantage because both the circulation and treatment of the recycle gas and the units for cleaning the waste gases can be made smaller.

By the term "structured reactor" is meant an arrangement of reaction channels which can be operated individually, in modules or even all together and which are disposed in a matrix intended for stabilization, security, heating or cooling. A preferred embodiment of a structured reactor are microreaction systems which are also known generally as microreactors or μ-reactors. Their characteristic feature is that at least one of the three spatial dimensions of the reaction space has a measurement in the range from 1 to 2000 μm so that the reactors are distinguished by a high transfer-specific inner surface, short residence times of the reactants and high specific heat and mass transfer levels. A detailed account on this subject is presented, for example, by Jähnisch et al. in Angewandte Chemie, Vol. 116, 410-451 (2004). Reference is made, by way of example, to European patent application EP 0903174 A1 (Bayer), which describes the liquid phase oxidation of organic compounds in a microreactor consisting of a bundle of parallel reaction channels. Microreactors may additionally contain microelectronic components as integral constituents. In contrast to known microanalytical systems, there is no need at all in microreactors for all lateral dimensions of the reaction space to be in the μm range. Rather, its dimensions are determined solely by the nature of the reaction. Accordingly, certain reactions may even be carried out in microreactors where a certain number of microchannels are bundled, so that microchannels and macrochannels can be present alongside one another, or a plurality of microchannels can be operated in parallel. The channels are preferably arranged parallel to one another in order to provide for high throughputs and to minimize the pressure loss.

Carriers

The carriers in which the structure and dimensions of the microreaction systems are predetermined may represent combinations of materials such as, for example, silicon/silicon, silicon/glass, glass/glass, metal/metal, metal/plastic, plastic/plastic or ceramic/ceramic, or combinations thereof, although the preferred embodiment is a silicon/glass combination. The structuring of a, for example, 100 to 2000 μm thick, preferably ca. 400 μm thick, wafer is preferably carried out by suitable microstructuring or etching techniques, for example, reactive ion etching, so that three-dimensional structures can be produced, for example, in silicon, irrespective of the crystal orientation [cf., Angell et al. in Sci. Am. 4, 248 (1993)]. Microreactors of glass, for example, can also be treated in the same way. Wafers thus treated can comprise 10 to 1000, preferably 100 to 500 and, more particularly, 200 to 300 parallel microreaction channels which can be actuated and operated either in parallel or sequentially. The geometry, i.e., the two-dimensional profile, of the channels can be very different: straight lines, curves, angles and the like, and combinations of these geometric elements are possible. Nor do all microreaction channels have to have the same geometry. The structures are distinguished by dimensions of 10 to 1500 μm, and preferably 20 to 1000 μm, and vertical walls, the depth of the channels being from 20 to 1800 μm, and preferably from ca. 200 to 500 μm. The cross-sections of each microreaction space, which may, but do not have to, be square, are generally of the order of 20×20 μm (approximately 400 μm$^2$) to about 1500× about 1800 μm (approximately 2.7×10$^{-6}$ m$^2$) and more particularly about 100× about 100 (approximately 10$^{-8}$ m$^2$) to about 300× about 300 μm (approximately 9×10$^{-8}$ m$^2$), as also stated to be typical, for example, by Burns et al. in Trans I ChemE 77(5), 206 (1999). To supply the microreaction spaces with the educts, the wafer is etched through at the intended places.

Finally, the structured wafer is bonded to another wafer, for example of glass, preferably Pyrex glass, by a suitable technique, for example, anodic bonding, and the individual flow channels are closed tightly with respect to one another. Depending on the substrate material, other building and bonding techniques for forming fluid-tight flow systems may, of course, also be applied by the expert without his/her becoming involved in any inventive activity to that end.

Structuring of the Microreactors

The microreaction systems may be divided into one or more mixing zones, one or more reaction zones, one or more mixing and reaction zones, one or more heating and cooling zones, or combinations thereof. They preferably comprise three zones, namely two reaction zones and one cooling zone, so that above all reactions involving two or more stages may be efficiently carried out in the liquid phase or even in the gas phase. In the first zone, two reactants are mixed and reacted; in the second zone, the reaction between the product of the first zone and another educt takes place and, in the third zone, the reaction is terminated by lowering the temperature. It is not absolutely essential for the first and second reaction zones to be strictly separated from one another in the thermal sense. This is because, if another reactant has to be added, or if several mixing points are required instead of just one, this can also be done beyond zone 1, in reaction zone 2. The microreaction channels may be operated sequentially or simultaneously, i.e., in parallel; with defined quantities of educt, and may have the same or different geometries. Another way in which the microreaction systems can differ in their geometry lies in the mixing angle at which the educts impinge on one another and which may be between 15 and 270° and preferably between 45 and 180°. In addition, each of the three zones may be cooled or heated independently of one another, or the temperature in a zone may be varied, as required, the reaction spaces in this example representing channels with a length per zone of 10 to 500 mm.

As explained at the beginning, the ozonolysis divides into two steps, namely formation of the ozonides and then their oxidative or reductive degradation. Accordingly, in practice, it is recommended to carry out the reaction as a whole in two structured reactors arranged in tandem. The reaction of the unsaturated compound with ozone takes place in the first reactor. The ozonides formed are then introduced into the second microreactor where, for example, they are oxidized with air or reduced with hydrogen in the presence of a catalyst, or by another suitable reducing agent, such as, for example, zinc in glacial acetic acid or sodium hydrogen sulfite. The reaction may be carried out with or without dilution by inert solvents.

Ozonolysis of Unsaturated Starting Materials

Basically, the choice of the unsaturated starting materials is not critical; on the contrary, it is another advantage of the process that it can be applied to very different substrates. Accordingly, the following selection of suitable starting materials should be regarded as preferred and illustrative, but not as limiting. Typical examples are:

aliphatic $C_{4-40}$ and preferably $C_{6-18}$ hydrocarbons containing 1 to 4 double bonds, such as, for example, the position-isomeric butenes, pentenes, hexenes, heptenes, octenes, decenes, dodecenes, tetradecenes, octadecenes, or butadiene, hexadiene, octadiene and the like;

$C_{4-40}$ and preferably $C_{16-22}$ mono- and dicarboxylic acids containing 1 to 4 double bonds, such as, for example, palmitoleic acid, elaidic acid, linoleic acid, linolenic acid, gadoleic acid, behenic acid, clupanodonic acid and, more particularly, oleic acid and maleic and fumaric acid;

esters of the above-mentioned mono- and dicarboxylic acids with $C_{1-10}$ alcohols or polyols, more particularly those with methanol, ethanol, n-propyl alcohol, isopropyl alcohol, the isomeric butanols, pentanols, hexanols, octanols, decanols, pentaerythritol, trimethylol propane and, more particularly, alkylene glycols and glycerol. The alcohol component may also be unsaturated, as, for example, with allyl alcohol. In this case, the carboxylic acid may even be saturated. However, particularly-preferred representatives of this group are unsaturated triglycerides, which can be obtained, in particular, from vegetable raw materials, such as, for example, low-unsaturated oils (for example, coconut oil or palm oil), medium-unsaturated oils (for example, olive oil), or highly unsaturated oils (for example, linseed oil, sunflower oil, rapeseed oil or thistle oil).

Basically, the reactants may be used in a stoichiometric molar ratio, the instability of the ozone having to be taken into account. However, one particular advantage of the process is that any mixtures of ozone, oxygen and unsaturated substrate, and also solvent, may be used because, even in the event of an explosion, flames extinguish spontaneously, if the dimensions of the microreaction systems are under the limiting gap width. Accordingly, ozone concentrations in the starting gas of 2 to 13% are preferred. Higher ozone concentrations are generally not available on an industrial scale. The principal constituent of the starting gas for the ozonolysis is oxygen, from which the ozone is produced. In addition, however, it is also possible to use a mixture with other gases as the starting gas for producing the ozone or to add that mixture after production of the ozone.

In order to reduce the viscosity of the ozonides formed, the reactants, as already mentioned, are generally diluted with a solvent. Basically, this can be done in any ratio, although a ratio of unsaturated reactant to solvent of 1:2 to 2:1 is preferred.

Ozonolysis

The reaction of ozone and the unsaturated reactants normally takes place at low temperatures, between −40° C. and 60° C., the range between 10° and 30° C. being preferred. The reaction may be carried out either in the absence of pressure, or under pressures of 1 to 25 bar, and, more particularly, 1 to 5 bar.

Oxidative Cleavage

The oxidative cleavage of the ozonization products generally takes place at temperatures of 20° to 140° C. and preferably at temperatures of 80° to 100° C. either in the absence of pressure, or under a slight excess pressure, preferably in the range of from about 1 to about 10 bar. Oxygen or an oxygen-containing gas stream is normally used for the oxidation. The reaction is generally carried out in the presence of a catalyst, metal salts and immobilized heterogeneous catalysts being used. The reactants are also generally present in dilute form.

Reductive Cleavage

The reductive cleavage of the ozonization products generally takes place at temperatures of 20° to 100° C. and preferably at temperatures of 50° to 80° C., in the absence of pressure, or under excess pressure, preferably in the range of from 1 to 10 bar. The reaction is carried out with a suitable reducing agent, preferably hydrogen or a hydrogen-containing gas stream. The reduction is preferably carried out in the presence of a metallic catalyst, particularly palladium.

Each of the three process steps of ozonolysis, oxidative and reductive cleavage can be carried out independently or in combination with at least one of the other two. More particularly, the reaction may also be carried out within the explosion limits of the liquid reactants and the gas mixture providing the dimensions of the microreaction system are under the limiting gap width.

The following Examples are for illustrative purposes only and should not be interpreted as limitations on this invention.

EXAMPLES

Example 1

Oxidative Ozonolysis of Oleic Acid

A micro falling-film reactor was used for the first part of the reaction, the reaction of ozone and oleic acid. The system consisted of 64 channels with a channel width and a channel depth of 300 μm and a channel length of 75 mm. The channels were operated in parallel and were etched through for educt input and product removal. The cooling channels corresponded in their diameter to the reaction channels. By virtue of the construction of the microreactor, contact between gas and liquid took place solely in the cooled region. The reaction was carried out in countercurrent, although co-current operation is also possible.

Technical oleic acid with the following composition was used for the ozonolysis: 5% palmitoleic acid (C16:1-FA), 69% oleic acid (C18:1-FA), 13% linoleic acid (C18:2-FA), 1% linolenic acid (C18:3-FA) and 1% gadoleic acid (C20:1). The other constituents were generally fatty acids with a chain length of $C_{12}$ to $C_{20}$. To dilute the reactants, the technical oleic acid was mixed with pelargonic acid in a ratio of 1:2.

Owing to their instability, the ozonization products were directly reacted and cleaved with oxygen in microreactors. In such a fixed-bed microreactor consisting of 50 parallel, 70 mm-long reaction channels, with a diameter of 600 μm, with 25 μm thick filters at the outlet of the microchannels, providing for retention of the catalyst powder, having particle diameters of 50 to 80 μm, using zeolite activated with manganese, as described in International Published Application WO 95/21809 A1, the reaction was carried out at 95° C., the reactor being heated with thermal oil. In view of the residence time required, two reactors of this type were arranged in tandem. The reactors for the second reaction step were operated in co-current (trickle flow) with oxygen, the mass ratio between ozonization products and oxygen being adjusted to 90:10. However, countercurrent operation is also possible. In all tests, ca. 0.3 Nl/h oxygen was used per reactor. The heat of reaction was dissipated through the thermal oil.

Both reaction steps were carried out continuously. The first reaction step took place at 20° C. 0.1 ml/min. of the liquid fatty acid mixture was used. The quantity of starting gas was varied according to the ozone concentration and the unreacted ozone was catalytically destroyed.

The ozonolysis of technical oleic acid was carried out in the first microreaction system. In the second microreaction system, the ozonization products formed were cleaved under the effect of oxygen to form a mixture, with the principal constituents being azelaic and pelargonic acid. The results are set out in Table 1 (recording the mean values of three measurements). The yield of azelaic acid is based on the total input of the technical oleic acid used, i.e., including the saturated constituents. The volume/time yield is based on the empty volumes of the reactors used.

The reaction mixture was analyzed by GC. Only minute traces of oleic acid were detected, so that the conversion under the selected conditions in the first reaction step can be regarded as a full conversion. After leaving the second oxidation reactor, ozonides could no longer be detected either. To monitor the GC analyses, relatively large quantities, from repeated test runs, were worked up as follows: the pelargonic acid was first distilled off and the azelaic acid was extracted with water and crystallized, yellowish crystals being obtained. After a recrystallization step, white crystals were obtained. The melting point was between 103° and 105° C., i.e., close to that of pure azelaic acid. GC analysis revealed purities of 97 to 99%.

The yield of azelaic acid, based on the quantity of technical oleic acid used, was between 51.5 and 52.7% of the theoretical and, by virtue of the excellent dissipation of heat, was almost independent of the ozone concentration in the starting gas. The yield, and hence the selectivity, for azelaic acid exceeded those of conventional processes for the selected starting composition.

TABLE 1

Test results (variation of the ozone concentration in the first reaction stage, oxidation under identical conditions at 95° C. in a fixed-bed microreactor)

| Parameter | 1 | 2 | 3 | 4 | 5 |
|---|---|---|---|---|---|
| Ratio of oleic to pelargonic acid [kg/kg] | 1:2 | 1:2 | 1:2 | 1:2 | 1:2 |
| Starting fatty acid [ml/min] | 0.1 | 0.1 | 0.1 | 0.1 | 0.1 |
| c(ozone) in the starting gas [%] | 2 | 5 | 7 | 10 | 13 |
| Starting gas [Nl/h] | 8.5 | 3.4 | 2.4 | 1.7 | 1.3 |
| Temperature [° C.] | 20 | 20 | 20 | 20 | 20 |
| Pressure [bar] | 1.3 | 1.3 | 1.3 | 1.3 | 1.3 |
| Residence time [s] | 120 | 120 | 120 | 120 | 120 |
| Yield of azelaic acid [%] | 51.5 | 52.1 | 52.5 | 52.7 | 52.3 |
| Volume/time yield [t·h$^{-1}$·m$^{-3}$]* | 1.12 | 1.13 | 1.14 | 1.14 | 1.13 |
| Volume/time yield [t·h$^{-1}$·m$^{-3}$]** | 0.26 | 0.26 | 0.27 | 0.27 | 0.27 |

*Yield of azelaic acid, based on the volume of the falling-film absorber
**Yield of azelaic acid, based on the volume of the falling-film absorber and the two following oxidizers In addition, the reactor can also be operated with high ozone concentrations in the starting gas, so that the quantity of starting gas can be significantly reduced.

Basically, the two reaction steps may also be carried out using other types of microstructured reactors and, hence, other flow forms of which the choice is immediately apparent to the expert and, hence, is not a limitation on the scope of protection of the invention. The two steps may be carried out independently of one another in one or more microreactors, a particular advantage in view of the instability of the ozonides lying in a direct linkage for a low specific holdup.

Example 2

Reductive Ozonolysis of Oleic Acid

The same micro falling-film reactor, as described above, was used for the first reaction step of the reductive ozonolysis, the operating parameters, listed in column 4 (Table 1), being adjusted. The ozonization products were again directly reacted in a following microreactor. The reactor used for the reduction was a palladium-coated film reactor. The reactor consisted of 64 channels with a width of 300 μm, a depth of 100 μm, and a length of 75 mm. Hydrogen was used in countercurrent for the hydrogenating cleavage of the ozonides. Azelaic acid semialdehyde and pelargonic aldehyde were mainly formed as products. The products were analyzed by GC. The second reaction step was carried out at 30° C./5 bar pressure. A test was carried out with 0.25 Nl/h hydrogen, the yield of azelaic acid semialdehyde being on average 48.7%.

Basically, the two reaction steps may also be carried out using other types of microstructured reactors and, hence, other flow forms of which the choice is immediately apparent to the expert and, hence, is not a limitation on the scope of protection of the invention. The two steps may be carried out independently of one another in one or more microreactors, a particular advantage in view of the instability of the ozonides lying in a direct linkage for a low specific holdup.

What is claimed is:

1. A process for the preparative ozonolysis of unsaturated starting materials, comprising reacting unsaturated compounds selected from the group consisting of aliphatic $C_4$-$C_{40}$ hydrocarbons, $C_4$-$C_{40}$ monocarboxylic acids, esters of $C_1$-$C_{10}$ alcohols or polyols with $C_4$-$C_{40}$ monocarboxylic acids, $C_4$-$C_{40}$ dicarboxylic acids, and esters of $C_1$-$C_{10}$ alcohols or polyols with $C_4$-$C_{40}$ dicarboxylic acids, with ozone in a microreaction system applied to a support, wherein said support comprises 10 to 1000 microreaction channels running parallel to one another, which channels may be actuated sequentially or simultaneously with the starting materials, to form ozonization products, wherein said unsaturated compounds contain 1 to 4 double bonds, and wherein said ozonization products are immediately subjected to oxidative cleavage by using an oxygen-containing gas stream, or, alternatively, to reductive cleavage by using a hydrogen-containing gas stream.

2. The process of claim 1, wherein the reaction channel diameter of said microreaction system does not exceed the limiting gap width.

3. The process of claim 1, wherein said microreaction system has at least one inlet for the starting materials and at least one outlet for the products.

4. The process of claim 1, wherein said support comprises a silicon/glass composite.

5. The process of claim 1, wherein said microreaction system is applied to said support by suitable microstructuring techniques.

6. The process of claim 1, wherein said microreaction channels have the same or different geometries.

7. The process of claim 1, wherein said microreaction channels have measurements of from 50 to 1500 μm in at least one spatial direction.

8. The process of claim 1, wherein said microreaction channels have a depth of from 20 to 1800 μm.

9. The process of claim 1, wherein said microreaction channels have cross-sections of about 400 μm$^2$ to about 2.7× 10$^{-6}$ m$^2$.

10. The process of claim 1, wherein said microreaction system comprises channels with a length of 1 to 1000 mm.

11. The process of claim 1, wherein said microreaction channels have one or more mixing zones, one or more reaction zones, one or more mixing and reaction zones, one or more heating or cooling zones, or any combinations thereof.

12. The process of claim 1, wherein said ozonolysis is carried out at a temperature in the range of −40° C. to 60° C.

13. The process of claim 1, wherein said ozonolysis is carried out in the absence of pressure, or under a pressure in the range of 1 to 25 bar.

14. The process of claim 1, wherein said ozonolysis is carried out with an ozone-containing gas mixture.

15. The process of claim 1, wherein, following ozonization of said unsaturated starting materials to create ozonization products, said ozonization products are subjected to oxidative cleavage, which is carried out in the presence of suitable catalysts at a temperature in the range of from 20° C. to 140° C.

16. The process of claim 15, wherein said oxidative cleavage of said ozonization products is carried out under a pressure in the range of 1 to 10 bar.

17. The process of claim 1, wherein, following ozonization of said unsaturated starting materials to create ozonization products, said ozonization products are subjected to reductive cleavage, which is carried out in the presence of one or more suitable catalysts at a temperature in the range of from 20° C. to 100° C.

18. The process of claim 17, wherein said reductive cleavage of said ozonization products is carried out under a pressure in the range 1 to 10 bar.

19. The process of claim 1, wherein, following ozonization of the unsaturated starting materials to create ozonization products, said ozonization products are subjected to oxidative cleavage, then to reductive cleavage in the same microreaction system.

20. A process for the decomposition of ozonides in a microreaction system, compromising subjecting said ozonides to oxidative cleavage at a temperature in the range of from 20° C. to 140° C. in the absence of pressure, or at a pressure in the range of from about 1 to about 10 bar, in the presence of one or more catalysts, followed by reductive cleavage at a temperature of from 20° C. to 100° C. in the absence of pressure, or at a pressure in the range of from about 1 to about 10 bar, in the presence of one or more catalysts.

* * * * *